US008741275B2

(12) United States Patent
Dente et al.

(10) Patent No.: US 8,741,275 B2
(45) Date of Patent: Jun. 3, 2014

(54) MALODOR NEUTRALIZING COMPOSITIONS COMPRISING UNDECYLENIC ACID OR CITRIC ACID

(75) Inventors: Stephen V. Dente, Englewood Cliff, NJ (US); Ketrin Leka, Bronx, NY (US); Brian Fielder, Leonia, NJ (US); Garry Johnson, Allendale, NJ (US)

(73) Assignee: Robetet, Inc., Mount Olive, NJ (US)

( * ) Notice: Subject to any disclaimer, the term of this patent is extended or adjusted under 35 U.S.C. 154(b) by 0 days.

(21) Appl. No.: 12/974,716

(22) Filed: Dec. 21, 2010

(65) Prior Publication Data

US 2011/0300095 A1 Dec. 8, 2011

Related U.S. Application Data

(60) Provisional application No. 61/351,435, filed on Jun. 4, 2010.

(51) Int. Cl.
*A61L 9/00* (2006.01)

(52) U.S. Cl.
USPC .............................................. 424/76.1; 560/1

(58) Field of Classification Search
None
See application file for complete search history.

(56) References Cited

U.S. PATENT DOCUMENTS

| | | | |
|---|---|---|---|
| 4,000,329 A | 12/1976 | Pittet et al. | |
| 4,009,253 A | 2/1977 | Schleppnik et al. | |
| 4,010,253 A | 3/1977 | Reese et al. | |
| 4,107,289 A | 8/1978 | Kaufman | |
| 4,310,152 A | 1/1982 | Mitzel | |
| 5,089,258 A | 2/1992 | Zaid | |
| 5,098,694 A | 3/1992 | Komp et al. | |
| 5,198,144 A | 3/1993 | Ichii et al. | |
| 5,202,124 A | 4/1993 | Williams et al. | |
| 5,451,346 A | 9/1995 | Amou et al. | |
| 5,554,588 A | 9/1996 | Behan et al. | |
| 5,589,164 A | 12/1996 | Cox et al. | |
| 5,662,937 A | 9/1997 | McCuaig | |
| 5,676,163 A | 10/1997 | Behan et al. | |
| 5,720,947 A | 2/1998 | Basset et al. | |
| 5,795,566 A | 8/1998 | Joulain et al. | |
| 5,800,897 A | 9/1998 | Sharma et al. | |
| 6,019,855 A | 2/2000 | Finch et al. | |
| 6,495,097 B1 | 12/2002 | Streit et al. | |
| 6,753,308 B1 | 6/2004 | Richardson et al. | |
| 6,906,045 B2 | 6/2005 | Ebube et al. | |
| 7,147,822 B2 | 12/2006 | Parkhurst et al. | |
| 7,157,411 B2 | 1/2007 | Rohde et al. | |
| 7,261,742 B2 | 8/2007 | Leskowicz | |
| 7,407,515 B2 | 8/2008 | Leskowicz | |
| 7,407,922 B2 | 8/2008 | Leskowicz | |
| 7,569,232 B2 | 8/2009 | Man et al. | |
| 7,638,118 B2 | 12/2009 | Flachsmann et al. | |
| 2002/0197287 A1 | 12/2002 | Streit et al. | |
| 2003/0113289 A1 | 6/2003 | Hu et al. | |
| 2004/0091595 A1 | 5/2004 | Dewis et al. | |
| 2004/0221858 A1 | 11/2004 | Higashi et al. | |
| 2006/0228250 A1 | 10/2006 | Brown et al. | |
| 2006/0287219 A1 | 12/2006 | Dykstra et al. | |
| 2007/0054815 A1 | 3/2007 | Convents et al. | |
| 2007/0231278 A1 | 10/2007 | Lee et al. | |
| 2008/0207481 A1 | 8/2008 | Meine et al. | |
| 2008/0221003 A1 | 9/2008 | Meine et al. | |
| 2010/0021413 A1 | 1/2010 | McGee et al. | |
| 2010/0028288 A1 | 2/2010 | Tranzeat et al. | |
| 2010/0034766 A1 | 2/2010 | McGee et al. | |
| 2010/0111889 A1* | 5/2010 | Marsh et al. ................. | 424/76.1 |
| 2011/0239736 A1 | 10/2011 | Ramji et al. | |
| 2011/0305659 A1 | 12/2011 | Woo et al. | |

FOREIGN PATENT DOCUMENTS

| | | |
|---|---|---|
| AU | 2009101152 | 1/2010 |
| DE | 3045483 A1 | 12/1982 |
| GB | 801726 A | 9/1958 |
| GB | 1311060 | 3/1973 |
| GB | 2187642 | 9/1987 |
| JP | 63-066115 | 3/1988 |
| JP | 7-291809 | 11/1995 |
| JP | 2000-282081 A | 10/2000 |
| WO | WO 97/15283 | 5/1997 |
| WO | WO 98/56889 | 12/1998 |
| WO | WO 00/27442 | 5/2000 |
| WO | WO 00/72890 | 12/2000 |
| WO | WO 03/051410 | 6/2003 |
| WO | WO 2006/102052 | 9/2006 |
| WO | WO 2006/131739 | 12/2006 |
| WO | WO 2011/152886 | 12/2011 |

OTHER PUBLICATIONS

International Search Report and Written Opinion mailed in corresponding application No. PCT/US2011/022697 on Jul. 5, 2012.
International Preliminary Report on Patentability issued in International Application No. PCT/US2011/022697 on Dec. 13, 2012.
International Search Report and Written Opinion mailed in corresponding International Application No. PCT/US2012/022209 on Apr. 4, 2012.
International Preliminary Report on Patentability mailed in corresponding International Application No. PCT/US2012/022209 on Aug. 8, 2013.
International Search Report dated Aug. 19, 2013 issued in related PCT Application No. PCT/US2013/033927.
International Search Report and Written Opinion mailed on Nov. 14, 2013 in International Application No. PCT/US2013/033927.
Matsubara, E., et al., "(−)-Bornyl acetate induces autonomic relaxation and reduces arousal level after visual display terminal work without any influences of task performance in low-dose condition," *Biomed Res* Apr. 2011; 32(2):151-7 (Abst).

* cited by examiner

*Primary Examiner* — Abigail Fisher
*Assistant Examiner* — Daniel L Branson
(74) *Attorney, Agent, or Firm* — Fish & Richardson P.C.

(57) ABSTRACT

Compositions comprising undecylenic acid or citric acid and certain esters are effective for reducing malodors. The esters are in the molecular weight range of between 150-200 when the acid is undecylenic acid and in the range of between 130-230 when the acid is citric acid. These compositions can be used in perfumed products, household products and personal care products.

37 Claims, No Drawings

MALODOR NEUTRALIZING COMPOSITIONS COMPRISING UNDECYLENIC ACID OR CITRIC ACID

CROSS-REFERENCE TO RELATED APPLICATION

This application claims the benefit of the filing date of U.S. Provisional Application No. 61/351,435, filed on 4 Jun. 2010. The contents of said provisional application are incorporated by reference in their entirety as part of this application.

FIELD OF THE INVENTION

This invention relates to odor neutralizer compositions and their use for reducing malodors.

BACKGROUND OF THE INVENTION

In many applicational areas, perfumes are used for masking malodors. Annoyance caused by malodors occurs frequently in daily life and impairs personal well-being. Such malodors are, for example, those resulting from substances transpired or excreted by humans, in particular, perspiration, mouth odors, feces and urine, odors caused by animal feces or urine, in particular, those of domestic pets, kitchen odors, such as those resulting from the preparation of onions, garlic, cabbage or fish, odors due to tobacco smoke, garbage, bathrooms, molds and waste.

In addition, malodors may be caused by many industrially produced basic materials used in cleansing agents, such as, for example, detergents and fabric softeners, or in body care products, such as, for example, soaps and cosmetics. The use of specific cosmetic preparations, such as, for example, hair dyes, hair-forming agents and depilatories, also produce malodors.

Many rubber and plastic products also produce malodors if, due to the method of their manufacture, they still contain quantities of highly odorous, volatile active ingredients. These malodors are usually caused by particularly odorous substances which are, however, generally only present in trace amounts. Such substances include, for example, nitrogen-containing compounds such as ammonia and amines, heterocyclic compounds such as pyridines, pyrazines, indoles, etc., and sulfur-containing compounds such as hydrogen sulfide, mercaptans, sulfides, etc.

The masking of malodors is a problem which is difficult to handle and solve with perfume compositions. Usually, it is only possible to mask malodors by means of a specially developed perfume oil having specific types of fragrances.

Malodor counteractings are particularly advantageous when they are capable of reducing the intensity of malodors without themselves possessing any significantly intense odor or fragrance. Such active ingredients do not mask malodors; rather, they neutralize the malodors. This has the advantage that, when using such active ingredients for perfuming objects or products having malodors, perfume oils of any desired type of fragrance can be used. The consumer can, therefore, be offered a considerably broader range of fragrance types for combating malodors.

In addition, active ingredients which neutralize malodors, provide the possibility of reducing the quantity of perfume oil previously required for masking odors. It is also possible to use less intensely odorous perfumes for combating malodors than those heretofore employed.

Another area in which malodor reducing compositions find utility is in breath freshening compositions such as chewing gum, mints, mouthwashes, lozenges and sprays. In addition to flavoring and perfuming ingredients which mask oral malodors, it is also useful to neutralize the ingredients which cause such malodors.

In recent years, a wide variety of substances have been proposed for use in neutralizing and/or suppressing malodors. These include certain acids such as undecylenic acid and a wide variety of esters, including esters of citric acid.

U.S. Pat. No. 6,495,097 describes the use of undecylenic acid and its lower alkyl esters as deodorants and odor neutralizers useful in a wide variety of compositions, perfumed and unperfumed. U.S. Pat. No. 4,010,253 discloses the use of certain esters of citric acid or acetylcitric acid in compositions for suppressing body odor. Citric acid itself has been used in personal deodorant compositions, as indicated in U.S. Pat. Nos. 5,098,694 and 5,662,937.

Recent patent literature disclosing the use of different classes of esters as malodor neutralizers include U.S. Pat. Nos. 7,157,411, 7,407,922 and 7,638,118, and Published Applications US 2010/0021413, US 2010/0028288 and US 2010/0034766.

Many of the esters disclosed in the prior art are quite effective in neutralizing malodors, and undecylenic acid (and its derivatives) has also shown some effectiveness in this area. It has now been discovered that combinations of undecylenic acid or citric acid and certain esters within particular molecular weight ranges have surprisingly shown synergistic effectiveness in neutralizing malodors.

SUMMARY OF THE INVENTION

This invention provides compositions comprising a combination of undecylenic acid or citric acid and one or more of certain esters within a particular molecular weight range. The molecular weight range for esters in combination with undecylenic acid is between 150 and 200. The molecular weight range for esters in combination with citric acid is between 130 and 230. These combinations exhibit a synergistic effect in neutralizing malodors. The esters within these particular molecular weight ranges which, in combination with undecylenic acid or citric acid, provide the synergistic effects are of the Formula (I) have the structure

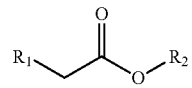

in which
  $R_1$ is hydrogen, phenyl substituted by hydroxy or an amino group, or a $C_1$-$C_{11}$ alkyl group which can optionally contain 1 or 2 double bonds and which optionally can be substituted by a phenyl group, and
  $R_2$ is $C_1$-$C_6$ unbranched alkyl, a $C_3$-$C_{12}$ branched alkyl group which can optionally contain 1 or 2 double bonds, or benzyl,
with the proviso that
  (i) where $R_1$ is a $C_1$-$C_{11}$ alkyl or alkylene radical substituted by phenyl, such substitution occurs at the 2- or higher carbon atom, and
  (ii) where both $R_1$ and $R_2$ are unbranched alkyls, the total number of carbon atoms in said alkyls is not greater than 12 and, if said total number of carbon atoms is greater than 8, the difference between the number of carbon atoms in $R_1$ and $R_2$ is at least 2.

The compositions of this invention can be admixed with fragrancing ingredients to yield perfumed products which also have malodor neutralizing affects. Additionally, these compositions can be incorporated into household products such as detergents and other laundry products, air fresheners and disinfectants. These compositions can also be incorporated into personal care products of all types.

DETAILED DESCRIPTION OF THE INVENTION

Undecylenic acid, citric acid and the esters of the Formula (I) are known odor neutralizers but it has now been discovered that a combination of undecylenic acid with at least one of said esters in the molecular weight range of between 150 and 200 provides a synergistic effect in odor neutralization. Likewise, it has now been discovered that compositions comprising a combination of citric acid and one or more ester of Formula (I) in the wider molecular weight range of between 130 and 230 provide a synergistic effect in odor neutralization.

The term "undecylenic acid" as used herein refers to undec-10-enoic acid of the formula.

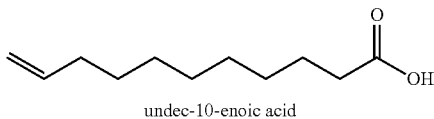

undec-10-enoic acid

It is used in the manufacture of pharmaceuticals, cosmetics and perfumery, including anti-dandruff shampoos, anti-microbial powders and as a musk in perfumes and aromas. U.S. Pat. No. 6,495,097 discloses its use, as well as the use of certain derivatives such as its methyl and ethyl esters, as substances that provide odor neutralization.

Citric acid (3-carboxy-3-hydroxypentanedioic acid) is used extensively in food products to add an acidic or sour taste and is also used in cleaning products. Additionally, as indicated in recent U.S. Pat. Nos. 6,906,045 and 7,147,822, citric acid can function as an odor neutralizer.

Citric acid has the formula

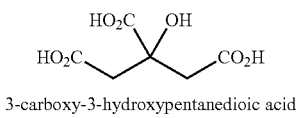

3-carboxy-3-hydroxypentanedioic acid

The esters which, in combination with undecylenic acid or citric acid are synergistically effective in neutralizing malodors have molecular weights within the specified particular ranges and have the structure (I)

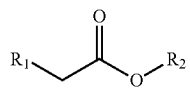

wherein
  $R_1$ is hydrogen, phenyl substituted by hydroxyl or an amino group, or a $C_1$-$C_{11}$ alkyl group which can optionally contain one or two double bonds and which optionally can be substituted by phenyl group, and
  $R_2$ is $C_1$-$C_6$ unbranched alkyl, a $C_3$-$C_{12}$ branched alkyl group which can optionally contain one or two double bonds, or benzyl, with the proviso that
  (i) where $R_1$ is a $C_1$-$C_{11}$ alkyl or alkylene radical substituted by phenyl, such substitution occurs at the 2- or higher carbon atom, and
  (ii) where both $R_1$ and $R_2$ are unbranched alkyls, the total number of carbon atoms in said alkyls is not greater than 12 and, if said total number of carbon is greater than 8, the difference between the number of carbon atoms in $R_1$ and $R_2$ is at least 2.

An example of $R_1$ as an alkylene radical substituted by phenyl at the 2-carbon is cinnamate. An example of an alkyl radical substituted at the 3-carbon is 3-phenylpropyl.

With respect to compounds in which both $R_1$ and $R_2$ are unbranched alkyls, butyl butyrate and ethyl heptanate, for example, would be within the scope of Formula (I). Pentyl hexanate is an example of a compound which would not be included in Formula (I). A preferred group of compounds in this class are those in which the total number of carbon atoms in $R_1$ and $R_2$ is not greater than 8.

In order to combat malodors, the combination of undecylenic acid or citric acid and the esters of Formula (I) may be used in admixture. They may be used in pure form or in suitable solvents such as, for example, ethanol, isopropanol or other solvents well known for use in deodorizing formulations.

The ratio of undecylenic acid or citric acid to the ester of Formula (I) can range between about 10% to 90%, preferably from about 25% to 75%. A weight ratio of about 50% is particularly preferred and convenient.

A preferred group of esters within the Formula (I) are those in which $R_2$ is $C_1$-$C_5$ (straight-chain or branched) alkyl or benzyl.

Preferred particular compounds within the Formula (I) for combination with undecylenic acid include the following:

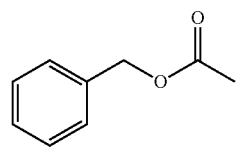

benzyl acetate

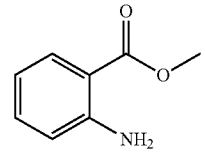

methyl anthranilate

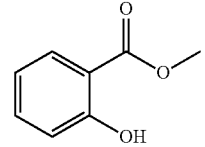

methyl salicylate

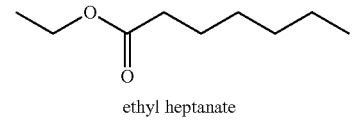

ethyl heptanate

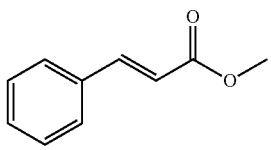

methyl cinnamate

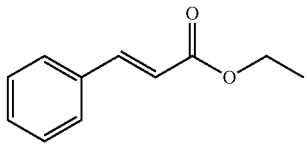

ethyl cinnamate

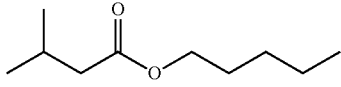

amyl isovalerate

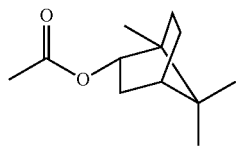

bornyl acetate

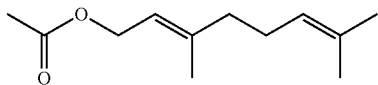

geranyl acetate

Preferred particular compounds within Formula (I) for combination with citric acid include, in addition to those preferred for combination with undecylenic acid, the following:

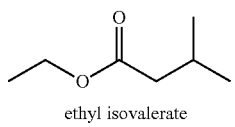

ethyl isovalerate

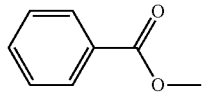

methyl benzoate

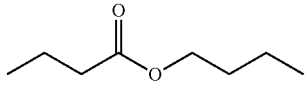

butyl butyrate

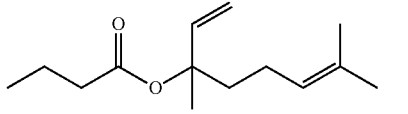

linalyl butyrate

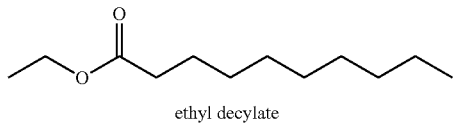

ethyl decylate

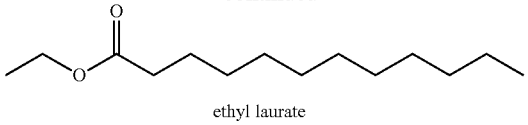

ethyl laurate

For odor neutralizing purposes, the compositions according to the present invention can be combined with one or more of a wide variety of fragrancing ingredients.

The following may be mentioned as examples of ingredients used in fragrancing compositions, in particular:

extracts from natural raw materials such as essential oils, resins, resinoids, balsams, tinctures such as for example ambergris tincture; amyris oil; angelica seed oil; angelica root oil; aniseed oil; valerian oil; basil oil; tree moss absolute; bay oil; armoise oil; benzoe resinoid; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oakmoss absolute; elemi oil; estragon oil; eucalyptus citriodora oil; eucalyptus oil (cineole type); fennel oil; fir needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil expressed; linaloe oil; Litsea cubeba oil; laurel leaf oil; mace oil; marjoram oil; mandarin oil; massoi (bark) oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil: spike-lavender oil; star anise oil; storax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniperberry oil; wine lees oil; wormwood oil; wintergreen oil; ylang-ylang oil; hyssop oil; civet absolute; cinnamon leaf oil; cinnamon bark oil; and fractions thereof or ingredients isolated therefrom;

individual fragrance ingredients from the group comprising hydrocarbons, such as for example 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols, such as for example hexanol; octanol; 3-octanol; 2,6-dimethyl-heptanol; 2-methyl-2-heptanol, 2-methyl-2-octanol; (E)-2-hexenol; (E)- and (Z)-3-hexenol; 1-octen-3-ol; a mixture of 3,4,5,6,6-pentamethyl-3,4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and their acetals such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal-diethylacetal; 1,1-dimethoxy-2,2,5-trimethyl-4-hexene; citronellyl oxyacetaldehyde;

aliphatic ketones and oximes thereof, such as for example 2-heptanone; 2-octanone; 3-octanone; 2-nonanone; 5-methyl-3-heptanone; 5-methyl-3-heptanone oxime; 2,4,4,7-tetramethyl-6-octen-3-one;

aliphatic sulfur-containing compounds, such as for example 3-methylthiohexanol; 3-methylthiohexyl acetate; 3-mercaptohexanol; 3-mercaptohexyl acetate; 3-mercaptohexyl butyrate; 3-acetyltbiohexyl acetate; 1-menthene-8-thiol;

aliphatic nitriles, such as for example 2-nonenenitrile; 2-tridecenenitrile; 2,12-tridecenenitrile; 3,7-dimethyl-2,6-octadienenitrile; 3,7-dimethyl-6-octenenitrile;

aliphatic carboxylic acids and esters thereof, such as for example (E)- and (Z)-3-hexenylformate; ethyl acetoacetate; isoamyl acetate; hexyl acetate; 3,5,5-trimethyl-hexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexylbutyrate; (E)- and (Z)-3-hexenyl isobutyrate; hexyl crotonate; ethylisovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate;

acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; α-sinensal; β-sinensal; geranylacetone; as well as the dimethyl- and diethylacetals of geranial, neral and 7-hydroxy-3,7-dimethyloctanal;

cyclic terpene alcohols, such as, for example, menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates of alpha-terpineol, terpinen-4-ol; methan-8-ol, methan-1-ol, methan-7-ol, borneol, isoborneol, linalool oxide, nopol, cedrol, ambrinol, vetiverol and guaiol;

cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alphadamascone; beta-damascone; beta-danascenone; deltadamascone; gamma-damascone; 1-(2,4,4-trimethyl-2-cyclohexen-1-yl)-2-buten-1-one; 1,3,4,6,7,8a-hexahydrol; 1,1,5,5-tetramethyl-2H-2,4-a-methanonaphthalen-8(5H)-one; nootkatone; dihydronootkatone; acetylated cedarwood oil (cedryl methyl ketone);

cyclic alcohols, such as, for example, 4-tert.-butylcyclohexanal; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols, such as, for example, alpha-3,3-trimethylcyclo-hexyl-methanol; 2-methyl-4-(2,2,3-trimethyl-3-cyclopent-1-yl)-butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)-pentan-3-ol; 1-(2,2,6-trimethylcyclohexyl)-hexan-3-ol;

cyclic and cycloaliphatic ethers, such as, for example, cineole; cedryl methyl ether; cyclododecyl methyl ether; (ethoxymethoxy)-cyclododecane; alpha-cedrene epoxide; 3a,6,6,9a-tetramethyldodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methyl-propyl)-1,3-dioxan;

cyclic ketones, such as, for example, 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

cycloaliphatic aldehydes, such as, for example, 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl)-ketone;

esters of cyclic alcohols, such as, for example, 2-tert.butylcyclohexyl acetate; 4-tert.-butylcyclohexyl acetate; 2-tert.-pentylcyclohexyl acetate; 4-tert.-pentylcyclohexyl acetate; decahydro-2-naphthyl acetate; 3-pentyltetrahy-dro-2H-pyran-4-yl acetate; decahydro-2,5,5,8a-tetramethyl-2-naphthyl acetate; 4,7-methano-3a,4,5, 6,7,7a-hexa-hydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

esters of cycloaliphatic carboxylic acids, such as, for example, allyl 3-cyclohexyl-propionate; allyl cyclohexyl oxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenyl ethyl alcohol; 1,1dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers, such as for example 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethyl-proparral; 2-methyl-3-(4-isopropylphenyl)-propanal; 2-methyl-3-(4-tert.-butylphenyl)propanal; 3-(4-tert.-butyl-phenyl)propanal; cinnamaldehyde; alpha-butyl-cinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene-dioxybenzaldehyde; 3,4-dimethoxybenzaldehyde; 2-methyl-3-(4-methoxyphenyl)-propanal; 2-methyl-3-(4-methylendioxyphenyl)-propanal;

aromatic and araliphatic ketones, such as, for example, acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert.-butyl-1,1,1-dimethyl-4-indanyl methyl ketone; 1-[2,3-dihydro-1,1,2,6-tetramethyl-3-(1-methyl-ethyl)-1H-5-indenyl]ethanone; 5',6',7',8'-tetrahydro-3',5',5',6',8',8'-hexamethyl-2-acetonaphthone;

aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

nitrogen-containing aromatic compounds, such as, for example, 2,4,6-trinitro-1,3-dimethyl-5-tert-butylbenzene; 3,5-dinitro-2,6-dimethyl-4-tert.-butylacetophenone; cinnamonitrile; 5-phenyl-3-methyl-2-pentenonitrile; 5-phenyl-3-methylpentanonitrile; methyl anthranilate; methyN-methylanthranilate; Schiff's bases of methyl anthranilate with 7-hydroxy-3,7-dimethyloctanal, 2-methyl-3-(4-tert.-butylphenyl)-propanal or 2,4-dimethyl-3-cyclohexene carbaldehyde; 6-isopropylquinoline; 6-isobutylquinoline; 6-sec.-butylquinoline; indole; skatole; 2-methoxy-3-isopropyl-pyrazine; 2-isobutyl-3-methoxypyrazine;

phenols, phenyl ethers and phenyl esters, such as, for example, estragole; anethole; eugenol; eugenyl methyl ether; isoeugenol; isoeugenol methyl ether; thymol; carvacrol; diphenyl ether; beta-naphthyl methyl ether; betanaphthyl ethyl ether; beta-naphthyl isobutyl ether; 1,4-dimethoxybenzene; eugenyl acetate; 2-methoxy-4-methylphenol; 2-ethoxy-5-(1-propenyl)-phenol; p-cresyl phenylacetate;

heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

The foregoing lists include some esters that fall within the scope of Formula (I), in which cases, a product comprising the composition of this invention will contain two or more of such esters.

In addition, the odor neutralizers containing the esters according to the present invention can be adsorbed onto a carrier which ensures both the fine distribution of the odor neutralizer in the product and controlled release during use. Such carriers can be porous inorganic materials such as light sulfates, salts, silica gels, borates, carbonates, soda ash, tripolyphosphates, zeolites, gypsums, clays, granulated clays, aerated concrete, etc., or organic materials such as wood, starches and other cellulose-based materials.

The odor neutralizers containing undecylenic acid or citric acid and the esters of Formula (I) can also be in microencapsulated or spray-dried form or in the form of inclusion complexes or extrusion products and they can be added in these forms to the product whose odor is to be improved or which is to be perfumed.

The compositions of the present invention may be added to a wide variety of consumer products, such as household products, personal care products and cosmetics, both perfumed and perfume-free, and both scented and scent-free.

Household products which may comprise a composition according to the invention include fabric washing powder and washing liquid, detergent, surface cleaner (including hard surface cleaner), air freshener in various forms (e.g., solids, gels, candles, liquids, etc.), softener, bleach, fabric refresher and room spray, disinfection products, scourer and cat litter. The list of household products is given by way of illustration and is not to be regarded as being in any way limiting.

Personal care products and cosmetics which may comprise a composition according to the invention include lotion, e.g. after-shave lotion, shampoo, conditioner, styling spray, mousse, gel, hair wipe, hair spray, hair pomade, bath and shower gel, bath salt, hygiene products, deodorant, antiperspirant, breath-freshening sprays, breath-freshening chewing gum, mouthwashes, lozenges and mints, vanishing cream, depilatory, and talcum powder. The list of personal care products and cosmetics is given by way of illustration and is not to be regarded as being in any way limiting.

Typically, the products using the composition of this invention comprise from about 0.0001% to about 20% by weight, preferably about 0.001% to about 10% by weight, of a combination of undecylenic acid or citric acid and at least one ester of Formula (I) based on the product. The effective amount depends upon the type of product into which the combination is admixed.

For example, if used in a fabric refresher the combination may be added to a fragrance composition at around 1% by weight which is then added to the product at around 0.1% by weight, i.e. the fabric refresher comprises about 0.001% by weight of the composition as hereinabove described. Or, in a liquid electrical air freshener composition, it may be added at higher concentration—typically around 20%—and may be present as 100% of the composition.

Accordingly, the present invention refers in a further aspect to a consumer product comprising an effective malodor-counteracting amount of a composition comprising undecylenic acid or citric acid and at least one ester of Formula (I).

Another aspect of the invention are methods of removing malodor from the air or from surfaces, comprising contacting the source of said malodor with an effective amount of a composition comprising undecylenic acid or citric acid and at least one ester of Formula (I) as hereinabove described. The methods can be, for example, spraying the ambient air surrounding the source of the malodors, or spraying an aerosol formulation directly onto the source of the malodor.

In a further aspect, the invention refers to a method of enhancing the malodor reduction properties of a consumer product, such as household products and personal care products, comprising admixing to the product effective amounts of at least undecylenic acid or citric acid and at least one ester of Formula (I) as hereinabove described.

Testing

Example I

A malodor evaluation panel of 14 persons was assembled and asked to evaluate the odor neutralizing effectiveness of undecylenic acid and of certain esters falling within the scope of Formula (I) in the molecular weight range of between 150 and 200, separately and in combination. The source of the malodor tested was cat urine.

Swatches of 100% untreated cotton fabric were cut into 15 cm (6-inch) squares and were placed on weighing boats. 0.5 grams of cat urine was pipetted onto each of the swatches. A period of three minutes was allowed for the urine to be absorbed by the fabric.

Onto each swatch, 3.0 grams of a composition was sprayed. As a control, 3.0 grams of water was sprayed on certain swatches.

Each swatch was placed in the middle of a 60 cm by 50 cm (2 feet by 2 feet) cubicle and all doors were closed. Actual testing was begun after thirty minutes.

Each member of the panel was asked to sniff the malodor control first and was notified that the control has a rating of 7—indicating very strong malodor. They were then asked to proceed to sniff the other samples and provide a rating for malodor remaining. Thus, the remaining malodor was evaluated on a sliding scale, with 1 being the absence of perceived malodor. The panelists were instructed to ignore any fragrance that they may detect and rate only for malodor.

For undecylenic acid alone and the ester of Formula (I) alone, the fabric sprays consisted of:
Test substance—1%
Neodol 91-8—1%
Fabric spray base—98%
For fabric sprays comprising both undecylenic acid and a subject ester, the formulation was:
Undecylenic acid—1%
Ester—1%
Neodol 91-8—2%
Fabric spray base—96.0%
Neodol 91-8 is a $C_9$-$C_{11}$ alcohol with an average of approximately 8 moles of ethylene oxide per mole of alcohol. The fabric spray base was an aqueous solution containing 10% ethanol, 1% of fragrance and 2% of non-ionic surfactant.

The results are shown in the following Table 1. Each panelist tested all of the esters, the undecylenic acid and the combination. The scores reported are therefore the average of 14 replications.

TABLE 1

| Ester | Molecular Weight | Score Alone (at 1%) | Score in comb. with Undecylenic Acid (1% + 1%) | Undecylenic Acid (at 1%) | Score alone – score in comb. | Undecylenic Acid – score in comb. |
|---|---|---|---|---|---|---|
| Benzyl Acetate | 150.174 | 2.64 | 1.94 | 3.03 | 0.69 | 1.08 |
| Methyl Anthranilate | 151.163 | 4.09 | 3.05 | 3.77 | 1.04 | 0.72 |
| Methyl Salicylate | 152.147 | 3.58 | 2.75 | 4.13 | 0.83 | 1.38 |
| Ethyl Heptanate | 158.238 | 3.41 | 2.56 | 3.80 | 0.85 | 1.24 |
| Methyl Cinnamate | 162.185 | 4.20 | 3.05 | 3.56 | 1.15 | 0.51 |

TABLE 1-continued

| Ester | Molecular Weight | Score Alone (at 1%) | Score in comb. with Undecylenic Acid (1% + 1%) | Undecylenic Acid (at 1%) | Score alone – score in comb. | Undecylenic Acid – score in comb. |
|---|---|---|---|---|---|---|
| Amyl Isovalerate | 172.264 | 4.55 | 3.40 | 3.70 | 1.15 | 0.30 |
| Ethyl Cinnamate | 176.212 | 3.46 | 2.47 | 4.17 | 0.99 | 1.70 |
| Bornyl Acetate | 196.286 | 2.40 | 1.94 | 3.50 | 0.45 | 1.56 |
| Geranyl Acetate | 196.286 | 3.86 | 3.24 | 4.08 | 0.62 | 0.84 |

Testing

Example II

Following the procedure of Example I, the odor neutralizing effectiveness of citric acid and of certain esters of Formula I in the molecular weight range of between 130 and 230 was evaluated. The results are shown in the following Table 2.

TABLE 2

| Ester | Molecular Weight | Score Alone (at 1%) | Score in comb. with Citric Acid (1% + 1%) | Citric Acid (at 1%) | Score alone – score in comb. | Citric Acid – score in comb. |
|---|---|---|---|---|---|---|
| Ethyl Isovalerate | 130.185 | 3.42 | 3.25 | 4.50 | 0.17 | 1.25 |
| Methyl Benzoate | 136.148 | 3.54 | 3.21 | 3.54 | 0.33 | 0.33 |
| Butyl Butyrate | 144.211 | 3.04 | 2.88 | 3.75 | 0.17 | 0.88 |
| Methyl Anthranilate | 151.163 | 4.00 | 3.29 | 4.43 | 0.71 | 1.14 |
| Methyl Cinnamate | 162.185 | 3.75 | 3.21 | 4.38 | 0.54 | 1.17 |
| Amyl Isovalerate | 172.265 | 3.86 | 3.55 | 4.05 | 0.32 | 0.50 |
| Bornyl Acetate | 196.286 | 3.95 | 1.77 | 4.00 | 2.18 | 2.23 |
| Geranyl Acetate | 196.286 | 3.27 | 3.00 | 4.36 | 0.27 | 1.36 |
| Ethyl Decylate | 200.318 | 3.62 | 2.96 | 3.88 | 0.65 | 0.92 |
| Linalyl Butyrate | 224.339 | 4.40 | 2.10 | 2.60 | 2.30 | 0.50 |
| Ethyl Laurate | 228.371 | 3.64 | 2.77 | 3.27 | 0.86 | 0.50 |

While the invention has been described in connection with preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

We claim:

1. A malodor neutralizing composition, comprising:
(1) undecylenic acid or citric acid, and
(2) at least one ester of the formula (I):

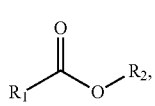

wherein
$R_1$ is hydrogen, phenyl optionally substituted by hydroxy or an amino group, or a $C_1$-$C_{11}$ alkyl group which can optionally contain 1 or 2 double bonds and which optionally can be substituted by a phenyl group, and
$R_2$ is $C_1$-$C_6$ unbranched alkyl, a $C_3$-$C_{12}$ branched alkyl group which can optionally contain 1 or 2 double bonds, or benzyl,
with the proviso that
(i) where $R_1$ is a $C_1$-$C_{11}$ alkyl or alkylene radical substituted by phenyl, such substitution occurs at the 2- or higher carbon atom, and
(ii) where both $R_1$ and $R_2$ are unbranched alkyls, the total number of carbon atoms in said alkyls is not greater than 12 and, if said total number of carbon atoms is greater than 8, the difference between the number of carbon atoms in $R_1$ and $R_2$ is at least 2,
said ester having a molecular weight of between 150 and 200 when ingredient (1) is undecylenic acid and a molecular weight of between 130 and 230 when ingredient (1) is citric acid, and
the amount of ingredient (2) is 50-90% by weight of the total amount of ingredients (1) and (2).

2. A malodor neutralizing composition according to claim 1 in which ingredient (1) is undecylenic acid and if, in ingredient (2), both $R_1$ and $R_2$ are unbranched alkyls, the total number of carbon atoms in said alkyls is not greater than 8.

3. A malodor neutralizing composition according to claim 2 in which, in ingredient (2), $R_2$ is $C_1$-$C_5$ unbranched alkyl or benzyl.

4. A malodor neutralizing composition according to claim 2 in which ingredient (2) is benzyl acetate, methyl anthranilate, methyl salicylate, ethyl heptanate, methyl cinnamate, ethyl cinnamate, amyl isovalerate, bornyl acetate or geranyl acetate.

5. A malodor neutralizing composition according to claim 4 in which ingredient (2) is bornyl acetate.

6. A perfumed product comprising a malodor neutralizing composition according to claim 2.

7. A perfumed product according to claim 6 in which ingredient (2) of the malodor neutralizing composition is benzyl acetate, methyl anthranilate, methyl salicylate, ethyl heptanate, methyl cinnamate, ethyl cinnamate, amyl isovalerate, bornyl acetate or geranyl acetate.

8. A household product comprising a malodor neutralizing composition according to claim 2.

9. A household product comprising a malodor neutralizing composition according to claim 8 in which ingredient (2) of the malodor neutralizing composition is benzyl acetate, methyl anthranilate, methyl salicylate, ethyl heptanate, methyl cinnamate, ethyl cinnamate, amyl isovalerate, bornyl acetate or geranyl acetate.

10. A personal care product comprising a malodor neutralizing composition according to claim 2.

11. A personal care product comprising a malodor neutralizing composition according to claim 10 in which ingredient (2) of the malodor neutralizing composition is benzyl acetate, methyl anthranilate, methyl salicylate, ethyl heptanate, methyl cinnamate, ethyl cinnamate, amyl isovalerate, bornyl acetate or geranyl acetate.

12. A malodor neutralizing composition according to claim 1 in which ingredient (1) is citric acid.

13. A malodor neutralizing composition according to claim 12 in which ingredient (2) is ethyl isovalerate, methyl benzoate, butyl butyrate, methyl anthranilate, methyl cinnamate, amyl isovalerate, bornyl acetate, geranyl acetate, ethyl decylate, or linalyl butyrate.

14. A malodor neutralizing composition according to claim 13 in which ingredient (2) is bornyl acetate.

15. A perfumed product according to claim 12 in which ingredient (2) of the malodor neutralizing composition is ethyl isovalerate, methyl benzoate, butyl butyrate, methyl anthranilate, methyl cinnamate, amyl isovalerate, bornyl acetate, geranyl acetate, ethyl decylate, or linalyl butyrate.

16. A household product comprising a malodor neutralizing composition according to claim 12.

17. A household product comprising a malodor neutralizing composition according to claim 16 in which ingredient (2) of the malodor neutralizing composition is ethyl isovalerate, methyl benzoate, butyl butyrate, methyl anthranilate, methyl cinnamate, amyl isovalerate, bornyl acetate, geranyl acetate, ethyl decylate, or linalyl butyrate.

18. A personal care product comprising a malodor neutralizing composition according to claim 12.

19. A personal care product comprising a malodor neutralizing composition according to claim 18 in which ingredient (2) of the malodor neutralizing composition is ethyl isovalerate, methyl benzoate, butyl butyrate, methyl anthranilate, methyl cinnamate, amyl isovalerate, bornyl acetate, geranyl acetate, ethyl decylate, or linalyl butyrate.

20. A method for reducing malodors which comprises contacting the source of said malodors with an effective amount of a malodor neutralizing composition comprising:

(1) undecylenic acid or citric acid, and
(2) at least one ester of the formula (I):

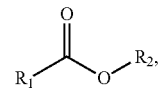

wherein
$R_1$ is hydrogen, phenyl optionally substituted by hydroxy or an amino group, or a $C_1$-$C_{11}$ alkyl group which can optionally contain 1 or 2 double bonds and which optionally can be substituted by a phenyl group, and
$R_2$ is $C_1$-$C_6$ unbranched alkyl, a $C_3$-$C_{12}$ branched alkyl group which can optionally contain 1 or 2 double bonds, or benzyl,
with the proviso that
(i) where $R_1$ is a $C_1$-$C_{11}$ alkyl radical substituted by phenyl, such substitution occurs at the 2- or higher carbon atom, and
(ii) where both $R_1$ and $R_2$ are unbranched alkyls, the total number of carbon atoms in said alkyls is not greater than 12 and, if said total number of carbon atoms is greater than 8, the difference between the number of carbon atoms in $R_1$ and $R_2$ is at least 2,
said ester having a molecular weight of between 150 and 200 when ingredient (1) is undecylenic acid and a molecular weight of between 130 and 230 when ingredient (1) is citric acid, and
the amount of ingredient (2) is 50-90% by weight of the total amount of ingredients (1) and (2).

21. A method according to claim 20 in which ingredient (1) of the malodor neutralizing composition is undecylenic acid and if, in ingredient (2), both $R_1$ and $R_2$ are unbranched alkyls, the total number of carbon atoms in said alkyls is not greater than 8.

22. A method according to claim 21 in which ingredient (2) of the malodor neutralizing composition is benzyl acetate, methyl anthranilate, methyl salicylate, ethyl heptanate, methyl cinnamate, ethyl cinnamate, amyl isovalerate, bornyl acetate or geranyl acetate.

23. A method according to claim 22 in which ingredient (2) of the malodor neutralizing composition is bornyl acetate.

24. A method according to claim 20 in which ingredient (1) of the malodor neutralizing composition is citric acid.

25. A method according to claim 24 in which ingredient (2) of the malodor neutralizing composition is ethyl isovalerate, methyl benzoate, butyl butyrate, methyl anthranilate, methyl cinnamate, amyl isovalerate, bornyl acetate, geranyl acetate, ethyl decylate, or linalyl butyrate.

26. A method according to claim 25 in which ingredient (2) is bornyl acetate.

27. A method for reducing malodors emanating from household or personal care products which comprises admixing to said products an effective amount of a malodor neutralizing composition comprising
(1) undecylenic acid or citric acid
(2) at least one ester of the formula (I):

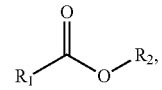

wherein

R$_1$ is hydrogen, phenyl optionally substituted by hydroxy or an amino group, or a C$_1$-C$_{11}$ alkyl group which can optionally contain 1 or 2 double bonds and which optionally can be substituted by a phenyl group, and R$_2$ is C$_1$-C$_6$ unbranched alkyl, a C$_3$-C$_{12}$ branched alkyl group which can optionally contain 1 or 2 double bonds, or benzyl, with the proviso that (i) where R$_1$ is a C$_1$-C$_{11}$ alkyl radical substituted by phenyl, such substitution occurs at the 2- or higher carbon atom, and (ii) where both R$_1$ and R$_2$ are unbranched alkyls, the total number of carbon atoms in said alkyls is not greater than 12 and, if said total number of carbon atoms is greater than 8, the difference between the number of carbon atoms in R$_1$ and R$_2$ is at least 2, said ester having a molecular weight of between 150 and 200 when ingredient (1) is undecylenic acid and a molecular weight of between 130 and 230 when ingredient (1) is citric acid, and the amount of ingredient (2) is 50-90% by weight of the total amount of ingredients (1) and (2).

28. A method according to claim 27 in which ingredient (1) of the malodor neutralizing composition is undecylenic acid and if, in ingredient (2), both R$_1$ and R$_2$ are unbranched alkyls, the total number of carbon atoms in said alkyls is not greater than 8.

29. A method according to claim 28 in which ingredient (2) of the malodor neutralizing composition is benzyl acetate, methyl anthranilate, methyl salicylate, ethyl heptanate, methyl cinnamate, ethyl cinnamate, amyl isovalerate, bornyl acetate or geranyl acetate.

30. A method according to claim 29 in which ingredient (2) of the malodor neutralizer composition is bornyl acetate.

31. A method according to claim 27 in which ingredient (1) of the malodor composition is citric acid.

32. A method according to claim 31 in which ingredient (2) of the malodor neutralizing composition is ethyl isovalerate, methyl benzoate, butyl butyrate, methyl anthranilate, methyl cinnamate, amyl isovalerate, bornyl acetate, geranyl acetate, ethyl decylate, or linalyl butyrate.

33. A method according to claim 32 in which ingredient (2) of the malodor neutralizing composition is bornyl acetate.

34. The malodor neutralizing composition of claim 1, wherein the composition comprises 2-20% of a combination of ingredients (1) and (2).

35. The method of claim 20, wherein the composition comprises 2-20% of a combination of ingredients (1) and (2).

36. The method of claim 27, wherein the composition comprises 2-20% of a combination of ingredients (1) and (2).

37. A malodor neutralizing composition, comprising:
(1) undecylenic acid or citric acid, and
(2) bornyl acetate or ethyl laurate,
wherein the amount of ingredient (2) is 50-90% by weight of the total amount of ingredients (1) and (2).

* * * * *

UNITED STATES PATENT AND TRADEMARK OFFICE
CERTIFICATE OF CORRECTION

PATENT NO.        : 8,741,275 B2                                                         Page 1 of 1
APPLICATION NO.   : 12/974716
DATED             : June 3, 2014
INVENTOR(S)       : Dente et al.

It is certified that error appears in the above-identified patent and that said Letters Patent is hereby corrected as shown below:

On the Title Page, Item [73]:

Delete "Robetet, Inc.," and insert --Robertet, Inc.,--.

In the Specification:

Column 2, lines 45-50:

Delete " 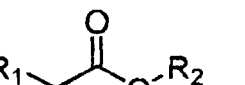 " and insert -- 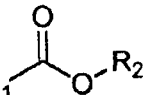 --.

In the Claims:

Column 15, line 44:

Claim 15, after "A perfumed product", insert --comprising the malodor neutralizing composition--.

Signed and Sealed this
Twenty-third Day of September, 2014

Michelle K. Lee
*Deputy Director of the United States Patent and Trademark Office*